United States Patent
Wiesler et al.

(10) Patent No.: US 7,828,271 B2
(45) Date of Patent: Nov. 9, 2010

(54) PROCESS FOR PREPARING ALKOXYPOLYOXYALKYLENE (METH) ACRYLATES

(75) Inventors: Uwe-Martin Wiesler, Darmstadt (DE); Joachim Knebel, Alsbach-Haehnlein (DE); Brigitte Mess, Muenster (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 12/159,871

(22) PCT Filed: Jan. 30, 2007

(86) PCT No.: PCT/EP2007/050875

§ 371 (c)(1), (2), (4) Date: Jul. 2, 2008

(87) PCT Pub. No.: WO2007/096228

PCT Pub. Date: Aug. 30, 2007

(65) Prior Publication Data

US 2009/0001322 A1   Jan. 1, 2009

(30) Foreign Application Priority Data

Feb. 23, 2006  (DE) .................. 10 2006 008 998

(51) Int. Cl.
C09K 15/08 (2006.01)
C08G 63/66 (2006.01)

(52) U.S. Cl. ...................... 254/404; 528/366

(58) Field of Classification Search .................. 252/404
See application file for complete search history.

(56) References Cited

U.S. PATENT DOCUMENTS 5,322,960 A   6/1994   Sakamoto et al.

(Continued)

FOREIGN PATENT DOCUMENTS

EP   0 765 856   4/1997

(Continued)

OTHER PUBLICATIONS

Williams et al. The Journal of Chemical Physics, 4,251 (1936).*

(Continued)

*Primary Examiner*—Melvin C Mayes
*Assistant Examiner*—Yun Qian
(74) *Attorney, Agent, or Firm*—Oblon, Spivak, McClelland, Maier & Neustadt, L.L.P.

(57) ABSTRACT

Process for preparing an alkoxypolyoxyalkylene (meth)acrylate in which a) a metal alkoxide $MetOR^{10}$ is initially charged,
b) an alkylene oxide of the formula (IV) is added and reacted with the metal alkoxide

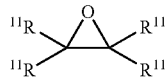

(IV)

and
c) (meth)acrylic anhydride is added directly and reacted with the reaction product from step b).

Appropriately, in step c), a stabilizer mixture is added which comprises, for example, the following components
I. at least one compound of the formula (I)

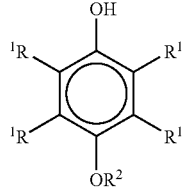

(I)

II. at least one compound of the formula (IIa or IIb)

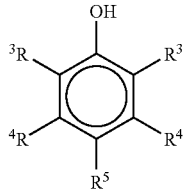

(II)

or of the formula (IV)

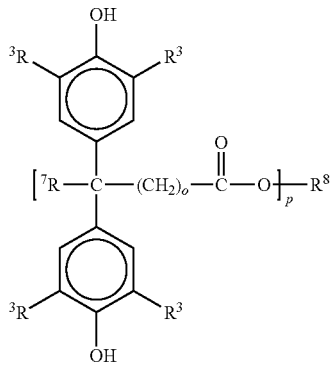

(IV)

III. at least one compound of the formula (V)

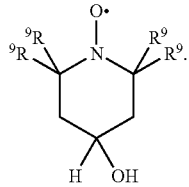

(V)

15 Claims, No Drawings

U.S. PATENT DOCUMENTS 6,458,956 B1 10/2002 Sutoris et al.
6,780,928 B1 * 8/2004 Itoh et al. .................. 524/599

FOREIGN PATENT DOCUMENTS

| EP | 0 976 716 | 2/2000 |
| EP | 1 086 939 | 3/2001 |
| FR | 2 739 850 | 4/1997 |
| WO | 01 74736 | 10/2001 |
| WO | 03 104301 | 12/2003 |
| WO | 2004 108795 | 12/2004 |

OTHER PUBLICATIONS

Jerry March, Advanced Organic Chemistry, Reactions, Mechanisms, and Structure, 4th Ed.1992.*
McMurry, Organic Chemistry, 6th Ed., 2002.*
U.S. Appl. No. 11/995,406, filed Jan. 11, 2008, Schmitt et al.
U.S. Appl. No. 12/088,093, filed Mar. 26, 2008, Schmitt et al.
U.S. Appl. No. 12/093,744, filed May 15, 2008, Schmitt et al.
U.S. Appl. No. 12/092,507, filed May 2, 2008, Klesse et al.
U.S. Appl. No. 61/014,927, filed Dec. 19, 2007, Karnbrock.

* cited by examiner

PROCESS FOR PREPARING ALKOXYPOLYOXYALKYLENE (METH) ACRYLATES

FIELD OF THE INVENTION

The present invention relates to a process for preparing alkoxypolyoxyalkylene (meth)acrylates, and to a stabilizer mixture which is particularly appropriate for this process.

STATE OF THE ART

DE 10 2004 042799 (BASF) describes the preparation of polyethylene glycol (meth)acrylates with catalysis by catalysts which, at 90 degrees Celsius, have a solubility in polyethylene glycol of not more than 10 g/litre. The catalysts used are hydroxides, oxides, carbonates or hydrogen carbonates of mono- or divalent alkali metals or alkaline earth metals.

Alkoxypolyoxyalkylene (meth)acrylates are already known and are proposed, for example, in the Patent Application EP 0 965 605 A2 (NOF Corporation) for the preparation of dispersants. The alkoxypolyoxyalkylene (meth)acrylates are prepared by adding a catalyst, for example p-toluenesulphonic acid monohydrate, to a polyoxyalkylene monoalkyl ether and subsequently performing an esterification with acrylic acid or methacrylic acid, by adding a catalyst, for example sodium methoxide, to a polyoxyalkylene monoalkyl ether and subsequently transesterifying with an alkyl acrylate, for example methyl acrylate, or with an alkyl methacrylate, for example methyl methacrylate, by reacting a polyoxyalkylene monoalkyl ether with acryloyl chloride or methacryloyl chloride, or by reacting a polyoxyalkylene monoalkyl ether with acrylic anhydride or methacrylic anhydride.

In EP 0 965 605 A2, Examples 7-11 and Comparative Examples 3 and 4 illustrate the preparation routes. In Examples 7, 9-11 and Comparative Examples 3 and 4, an alkoxide, for example sodium methoxide, is initially charged, reacted with an alkylene oxide, for example ethylene oxide, propylene oxide or an alkylene oxide mixture of propylene oxide and 1,2-butylene oxide, neutralized with hydrochloric acid and then esterified with acrylic acid or methacrylic acid in toluene with catalysis by p-toluenesulphonic acid. The stabilizer used is hydroquinone.

In Example 8 of the abovementioned application, sodium methoxide is reacted with ethylene oxide in methanol and neutralized with hydrochloric acid, and the product is isolated and dried, admixed again with sodium methoxide in methanol and transesterified with methyl methacrylate. The stabilizer added is t-butylhydroxy-toluene.

Even though the processes described above are suitable in principle for preparing alkoxypolyoxyalkylene (meth)acrylates, more efficient and less expensive routes to the preparation are nevertheless desirable.

PROBLEM AND SOLUTION

It is therefore an object of the present invention to specify an improved process for preparing alkoxypolyoxyalkylene (meth)acrylates. This process should enable the preparation of the alkoxypolyoxyalkylene (meth)acrylates in a particularly simple manner, on the industrial scale and inexpensively, in high quality and with acceptable reaction rates.

In the text which follows, the term (meth)acrylates means both acrylates and methacrylates, and also mixtures of the two compounds.

It has been found, surprisingly, that this object can be achieved by a process in which a reactor
a) is initially charged with at least one metal alkoxide MetOR$^{10}$,
b) at least one alcohol R$^{12}$OH is added,
c) at least one alkylene oxide of the formula (VI) is added and reacted with the metal alkoxide/alcohol mixture

d) then (meth)acrylic anhydride is added directly and reacted with the reaction product from step c) and then optionally with water.

The inventive procedure allows a "one-pot synthesis", i.e. an isolation and purification of intermediates is no longer required.

The present invention therefore relates to a process for preparing poly(oxyalkylene) monoacrylic esters and monomethacrylic esters by reacting acrylic anhydride or methacrylic anhydride (hereinafter (meth)acrylic anhydride A) with a reaction product formed from
d) at least one metal alkoxide MetOR$^{10}$
e) at least one alcohol R$^{12}$OH
f) at least one alkylene oxide of the formula (VI)

wherein the end product, after the reaction has ended, is optionally admixed with water, and the methacrylic anhydride is used in a molar ratio, based on the reaction product of the metal alkoxide MetOR$^{10}$, the alcohol R$^{12}$OH and the alkylene oxide of the formula (VI), which is between 1:1 and 3:1.

The process according to the invention is associated with a series of advantages. Firstly, separate provision of monofunctional polyoxyalkylene raw materials bearing OH groups is no longer necessary, and, secondly, shorter reaction times are achieved overall than in the method in two separate reactions, which is the current state of the art.

In addition, improved means of stabilizing the reaction mixture and the resulting product were to be indicated.

It has been found that, surprisingly, suitable selection of the stabilizers or of the stabilizer mixture, especially those which are water-soluble and unreactive toward methacrylic anhydride, considerably prolongs the stability time of the monomer.

This object and further objects which have not been described specifically but which can be discerned from the above-described connections are achieved by a process for preparing alkoxypolyoxyalkylene (meth)acrylates having all features of the present independent process claims. The dependent process claims describe particularly advantageous procedures for preparing alkoxypolyoxyalkylene (meth) acrylates. Further product claims protect a stabilizer mixture whose use in the present process is very particularly appropriate.

In the process according to the invention, at least one metal alkoxide MetOR$^{10}$ is first initially charged. The Met radical is lithium, sodium, potassium, rubidium or caesium, preferably lithium, sodium or potassium, in particular sodium or potassium, more preferably sodium. It is also possible for a metal hydroxide to be initially charged, in which case dewatering of the reaction solution before the addition of the alkylene oxide is required.

$R^{10}$ is a linear or branched alkyl radical, preferably having 1 to 18 carbon atoms, especially a methyl, ethyl, n-propyl, isopropyl, n-butyl, isobutyl, tert-butyl, n-pentyl, n-hexyl, n-heptyl, n-octyl, nonyl, decyl, undecyl, dodecyl, tridecyl, tetradecyl, pentadecyl, hexadecyl, heptadecyl or an octadecyl radical. $R^{10}$ may also be hydrogen.

Particular preference is given to a radical which has 1 to 4 carbon atoms.

$R^{12}$ is a linear or branched, optionally alkoxylated alkyl radical, preferably having 1 to 18 carbon atoms, in particular a methyl, 2-methoxyethyl, 2-(2-methoxyethoxy)ethyl, 2-(2-(2-methoxyethoxy)ethoxy)-ethyl, ethyl, n-propyl, isopropyl, n-butyl, isobutyl, tert-butyl, n-pentyl, n-hexyl, n-heptyl, n-octyl, nonyl, decyl, undecyl, dodecyl, tridecyl, tetradecyl, pentadecyl, hexadecyl, heptadecyl or an octadecyl radical, where the molar mass of $R^{12}$ is less than the molar mass of the inventive alkoxypolyoxyalkylenes. Particular preference is given to a radical which has 1 to 4 carbon atoms.

In the process according to the invention, at least one alkylene oxide of the formula (VI) is then added and it is reacted with the metal alkoxide.

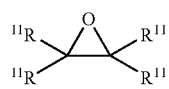

(VI)

The $R^{11}$ radicals are each independently hydrogen or a linear or branched alkyl radical, preferably having 1 to 8 carbon atoms, especially a methyl, ethyl, n-propyl, isopropyl, n-butyl, isobutyl, tert-butyl, n-pentyl, n-hexyl, n-heptyl or an n-octyl radical. A radical which has 1 to 4 carbon atoms is particularly preferred.

In this context, ethylene oxide, propylene oxide and 1,2-butylene oxide, and also mixtures of these compounds, have been found to be very particularly useful.

The reaction of the metal alkoxide with the alkylene oxide is preferably performed in a reactive solvent $R^{12}OH$. A particularly favourable solvent is the alcohol whose alkoxide is reacted with the alkylene oxide.

The length of the polyalkylene block can be adjusted via the molar ratio of metal alkoxide and alcohol $R^{12}OH$ on the one hand to alkylene oxide on the other. It is preferably in the range of 1:1-10 000, appropriately in the range of 1:1-1000, especially in the range of 1:1-100.

The reaction is appropriately performed at a temperature in the range of 60° C. to 150° C., preferably in the range of 80° C. to 120° C., especially in the range of 90° C. to 110° C.

The reaction time is preferably in the range of 1 to 20 hours, preferably in the range of 2 to 10 hours, especially in the range of 4 to 8 hours.

After the reaction, any excess alkylene oxide can be removed, for example by applying a reduced pressure.

The reaction product from the reaction of the metal alkoxide and alcohol with the alkylene oxide is reacted directly with (meth)acrylic anhydride, i.e. without isolating and/or purifying the intermediate. The expression (meth)acrylic anhydride encompasses both methacrylic anhydride and acrylic anhydride, and also mixtures of the two compounds.

In the context of the present invention, the (meth)acrylic anhydride, based on the sum of the metal alkoxide and the alcohol, is preferably used in excess, preferably in a molar ratio of (meth)acrylic anhydride to metal alkoxide of greater than 1, especially in the range of 1-3:1.

The reaction is appropriately performed at a temperature in the range of 60° C. to 150° C., preferably in the range of 70° C. to 110° C., especially in the range of 80° C. to 100° C.

The reaction time is preferably in the range of 1 to 20 hours, preferentially in the range of 2 to 10 hours, especially in the range of 4 to 8 hours.

The Stabilizers and the Stabilizer Mixtures

In addition, the reaction is appropriately performed in the presence of at least one stabilizer or one stabilizer mixture. In the context of the present invention, stabilizers (antioxidants) denote preferably organic compounds which are intended to prevent undesired polymerization of the methacrylic anhydride and/or of the alkoxypolyoxyalkylene (meth)acrylate. The action of the stabilizers usually consists in acting as free-radical scavengers for the free radicals which occur in the polymerization. For further details, reference is made to the common technical literature, especially to the Römpp-Lexikon Chemie; Editors: J. Falbe, M. Regitz; Stuttgart, New York; 10th edition (1996); under "Antioxidants", and the literature references cited at this point.

Stabilizers particularly suitable for the purposes of the present invention include tocopherol, tert-butylmethoxyphenol (BHA), butylhydroxytoluene (BHT), octyl gallate, dodecyl gallate, ascorbic acid, optionally substituted phenols, optionally substituted hydroquinones, for example hydroquinone monomethyl ether (HQME), optionally substituted quinones, optionally substituted pyrocatechols, optionally substituted aromatic amines, optionally substituted metal complexes of an aromatic amine, optionally substituted triazines, organic sulphides, organic polysulphides, organic dithiocarbamates, organic phosphites and organic phosphonates.

Substituted Phenols

Optionally substituted phenols are used with very particular preference in accordance with the invention. These preferably satisfy the formula (I)

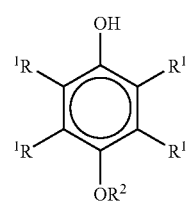

(I)

where the $R^1$ radicals are each independently hydrogen, a linear or branched alkyl radical, preferably having 1 to 8 carbon atoms, especially a methyl, ethyl, n-propyl, isopropyl, n-butyl, isobutyl, tert-butyl, n-pentyl, n-hexyl, n-heptyl or an n-octyl radical, which favourably has 1 to 4 carbon atoms, an optionally substituted cycloalkyl radical, preferably having 4 to 8 carbon atoms, especially a cyclohexyl radical, an optionally substituted aryl radical, preferably having 6 to 18 carbon atoms, or a halogen, preferably fluorine, chlorine or bromine, and where $R^2$ is a linear or branched alkyl radical, preferably having 1 to 8 carbon atoms, especially a methyl, ethyl, n-propyl, isopropyl, n-butyl, isobutyl, tert-butyl, n-pentyl, n-hexyl, n-heptyl or is an n-octyl radical, which more preferably has 1 to 4 carbon atoms, is an optionally substituted cycloalkyl radical, preferably having 4 to 8 carbon atoms, especially a cyclohexyl radical, or is an optionally substituted aryl radical, preferably having 6 to 18 carbon atoms.

Compounds (I) which are very particularly favourable in this context have hydrogen as $R^1$. $R^2$ is preferably an alkyl radical having 1 to 4 carbon atoms, especially a methyl radical.

It has also been found that compounds of the formula (II) are particularly useful for the purposes of the present invention

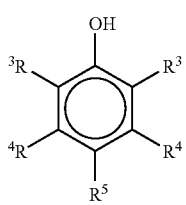
(II)

where the $R^3$, $R^4$ and $R^5$ radicals are each independently hydrogen, a linear or branched alkyl radical, preferably having 1 to 8 carbon atoms, especially a methyl, ethyl, n-propyl, isopropyl, n-butyl, isobutyl, tert-butyl, n-pentyl, n-hexyl, n-heptyl or an n-octyl radical, which more preferably has 1 to 4 carbon atoms, an optionally substituted cycloalkyl radical, preferably having 4 to 8 carbon atoms, especially a cyclohexyl radical, an optionally substituted aryl radical, preferably having 6 to 18 carbon atoms, a halogen, preferably fluorine, chlorine or bromine, or a radical of the formula (III)

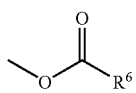
(III)

in which $R^6$ is a linear or branched alkyl radical having 1 to 6 carbon atoms, preferably a methyl, ethyl, n-propyl, isopropyl, n-butyl, isobutyl, tert-butyl, n-pentyl or n-hexyl radical, especially an ethyl radical.

Compounds (II) which are very particularly favourable in this context have hydrogen as $R^4$. $R^3$ is preferably an alkyl radical having 1 to 4 carbon atoms, especially a methyl radical. $R^5$ is appropriately an alkyl radical having 1 to 4 carbon atoms, especially a tert-butyl radical.

For the purposes of the present invention, compounds of the formula (IIa) have also been found to be suitable.

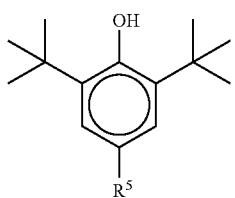
(IIa)

The compound of the formula (IIb) has also been found to be particularly favourable:

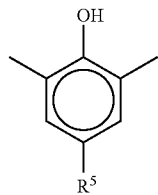
(IIb)

where: $R^5$=tert-butyl.

The compound is sold under the brand Topanol® A by Ciba.

In addition, favourable results can also be achieved using compounds of the formula (IV)

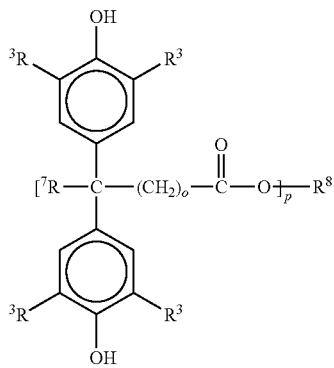
(IV)

where o is an integer in the range of 1 to 4 and p is 1 or 2, preferably 2,
where the $R^3$ radicals are each as defined above,
where $R^7$ is hydrogen or
a linear or branched alkyl radical, preferably having 1 to 8 carbon atoms, especially a methyl, ethyl, n-propyl, isopropyl, n-butyl, isobutyl, tert-butyl, n-pentyl, n-hexyl, n-heptyl or an n-octyl radical, especially a methyl radical, and
where $R^8$ is a monovalent alkyl group or divalent alkylene group, preferably a linear, α,ω-divalent alkylene group, preferably having 1 to 8 carbon atoms, especially a methyl, methylene, ethyl, 1,2-ethylene, n-propyl, 1,3-n-propylene, isopropyl, n-butyl, isobutyl, tert-butyl, 1,4-butylene, n-pentyl, 1,5-pentylene, n-hexyl, 1,6-hexylene, n-heptyl, 1,7-heptylene, n-octyl or a 1,8-octylene group, which more preferably has 1 to 4, most preferably 2, carbon atoms.

A particularly preferred compound of the formula (IV) is glycol bis[3,3-bis(4'-hydroxy-3'-tert-butylphenyl)-butanoate].

In a very particularly preferred embodiment of the present invention, a stabilizer mixture is used which comprises
a) at least one compound of the formula (I)
b) at least one compound of the formula (II) or (IV) and
c) at least one compound of the formula (V)

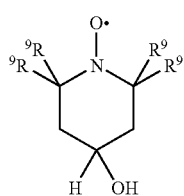
(V)

where the $R^9$ radicals are each independently a linear or branched alkyl radical, preferably having 1 to 6, especially having 1 to 4, carbon atoms, such as a methyl, ethyl, n-propyl, isopropyl, n-butyl, isobutyl or a tert-butyl radical, especially a methyl radical. The compound of the formula (V) is sold under the brand Tempol® by Ciba and under the name 4-hydroxy-2,2,6,6-tetramethylpiperidine 1-oxyl by Degussa GmbH.

The weight ratio of the compound (I) to the compound (II) or (IV) and to the compound (V) is preferably in the range of 1:0.1-25.0:0.01-1.0.

Based on the (meth)acrylic anhydride, the proportion of the stabilizers individually or as a mixture is preferably 0.001 to 2.0% by weight.

Owing to the hydrolysis sensitivity of the reactants, it is appropriate to work under substantially anhydrous conditions. Moreover, the reactants used are dried substantially completely. In addition, the use of an inert gas atmosphere, especially of dry nitrogen and/or argon in the performance of the alkoxylation step has also been found to be very particularly useful. In the subsequent reaction with (meth)acrylic anhydride, in contrast, oxygen should be present, either in a mixture with the inert gases mentioned or as a dry air atmosphere, in order to increase the stabilization against polymerization.

Possible fields of use of the alkoxypolyoxyalkylene (meth) acrylates are already known. They are suitable, inter alia, for preparing dispersants.

The invention will be illustrated in more detail hereinafter by several inventive examples, without any intention that it be restricted to these specific embodiments.

The length of the polyalkylene block was determined by withdrawing a small sample after step b) and determining the OH number.

EXAMPLES

Example 1

Apparatus: 2 l Büchi jacketed glass autoclave with manometer, mechanical stirrer, internal Pt 100 temperature sensor, inlet tube and oil circulation thermostat.

The reactor is evacuated, filled with nitrogen and charged with 6.6 g of a 30% solution of sodium methoxide in methanol (NM 30, Degussa AG). 6 g of dry methanol are added and the mixture is heated to 100° C., and 756 g of ethylene oxide are pumped in within 2 h, such that a pressure of 6 bar is not exceeded. Thereafter, reaction is allowed to continue at this temperature for a further 0.5 h. The mixture is cooled to 80° C. and unconsumed ethylene oxide is drawn off under reduced pressure (approx. 150 mbar) (time: approx. 0.5 h). A sample (10 g) is withdrawn for hydroxyl number determination, and 83.6 g of methacrylic anhydride which contain 3.4 g of hydroquinone monomethyl ether (HQME) and 0.17 g of 2,6-dimethyl-4-tert-butylphenol (Topanol® A) and 0.08 g of 4-hydroxy-2,2,6,6-tetramethylpiperidine 1-oxyl (Tempol®) in dissolved form are added to the reactor, and the mixture is heated at standard pressure with slow introduction of air to 90° C. for 6 h.

After cooling to room temperature, the reaction product is withdrawn, weighed and admixed with the same amount of water. 1700 g of an aqueous methacrylic acid-containing methoxypolyethylene glycol 2000 methacrylate solution are obtained.

Analytical Data:

OH number of the 10 g sample consisting of methoxypolyethylene glycol 2000: 27 mg KOH/g Determination of the Molar Mass:

M=(molar mass of potassium hydroxide)*100/(OH number)=5600/27=2074

| End product: | Water content: 50% (Karl-Fischer titration) |
| --- | --- |
| | Acid number: 23 mg KOH/g (titration) |
| | Hydroxyl number (calculated on dry substance): 1 mg KOH/g |
| | HQME content: 25 ppm (determined by liquid chromatography) |
| | Topanol A: 80 ppm (determined by liquid chromatography) |
| | Tempol: content below the detection limit |

The content of HQME has declined compared to the initial weight (2000 ppm based on aqueous product solution) as a result of side reactions, as has the Tempol content (initial weight 47 ppm based on aqueous product solution). Compared to this, the content of Topanol A is reduced only from 100 ppm to 80 ppm.

Example 2

As Example 1, except with use of 2.64 g of NM30 solution and 12.3 g of methyltriglycol instead of the methanol. Reaction is effected with 605 g of ethylene oxide in 1.5 h. After the sampling, 28 g of methacrylic anhydride which contains 2.5 g of HQME, 0.06 g of Tempol and 0.06 g of Topanol® A in dissolved form are added. After the reaction and water addition have ended, 1270 g of aqueous methoxypolyethylene glycol 5000 methacrylate solution are obtained.

Analytical Data:

OH number of the 10 g sample, consisting of methoxypolyethylene glycol 5000: 11 mg KOH/g

| End product: | Water content: 51% (Karl-Fischer titration) |
| --- | --- |
| | Acid number: 9.5 mg KOH/g (titration) |
| | Hydroxyl number (calculated on dry substance): 1.5 mg KOH/g |

Example 3

As Example 1, except with use of 13.2 g of NM30 solution and 12 g of methanol. Reaction is effected with 737 g of ethylene oxide in 2 h. After the sampling, 174 g of methacrylic anhydride which contains 3.7 g of HQME, 0.09 g of Tempol and 0.35 g of Topanol® A in dissolved form are added. After the reaction and water addition have ended, 1880 g of aqueous methoxypolyethylene glycol 1000 methacrylate solution are obtained.

Analytical Data:

OH number of the 10 g sample, consisting of methoxypolyethylene glycol 1000: 55 mg KOH/g

| End product: | Water content: 49% (Karl-Fischer titration)<br>Acid number: 43 mg KOH/g (titration)<br>Hydroxyl number (calculated on dry substance): 1 mg KOH/g |
|---|---|

Example 4

As Example 1, except with use of 18 g of NM30 solution and 16.5 g of methanol. Reaction is effected with 760 g of ethylene oxide in 2 h. After the sampling, 242 g of methacrylic anhydride which contains 4.2 g of HQME, 0.1 g of Tempol® and 0.5 g of Topanol® A in dissolved form are added. After the reaction and water addition have ended, 2080 g of aqueous methacrylic acid-containing methoxypolyethylene glycol 750 methacrylate solution are obtained.

Analytical Data:

OH number of the 10 g sample, consisting of methoxypolyethylene glycol 750: 75 mg KOH/g

| End product: | Water content: 50% (Karl-Fischer titration)<br>Acid number: 55 mg KOH/g (titration)<br>Hydroxyl number (calculated on dry substance): 2 mg KOH/g |
|---|---|

Example 5

As Example 1, except with use of 26.4 g of NM30 solution and 24 g of methanol. Reaction is effected with 737 g of ethylene oxide in 2 h. After the sampling, 359 g of methacrylic anhydride which contains 4.6 g of HQME, 0.1 g of Tempol® and 0.72 g of Topanol® A in dissolved form are added. After the reaction and water addition have ended, 2300 g of aqueous methacrylic acid-containing methoxypolyethylene glycol 500 methacrylate solution are obtained.

Analytical Data:

OH number of the 10 g sample, consisting of methoxypolyethylene glycol 500: 110 mg KOH/g

| End product: | Water content: 52% (Karl-Fischer titration)<br>Acid number: 76 mg KOH/g (titration)<br>Hydroxyl number (calculated on dry substance): 2.5 mg KOH/g |
|---|---|

Example 6

As Example 1, except with use of 39.6 g of NM30 solution and 36 g of methanol. Reaction is effected with 774 g of ethylene oxide in 2.5 h. After the sampling, 554 g of methacrylic anhydride which contains 5.6 g of HQME, 0.14 g of Tempol® and 1.11 g of Topanol® A in dissolved form are added. After the reaction and water addition have ended, 2800 g of aqueous methacrylic acid-containing methoxypolyethylene glycol 350 methacrylate solution are obtained.

Analytical Data:

OH number of the 10 g sample, consisting of methoxypolyethylene glycol 350: 155 mg KOH/g

| End product: | Water content: 50% (Karl-Fischer titration)<br>Acid number: 99 mg KOH/g (titration)<br>Hydroxyl number (calculated on dry substance): 2.1 mg KOH/g |
|---|---|

Example 7

As Example 1, except that, after the sampling, 70 g of acrylic anhydride which contains 3.3 g of HQME, 0.08 g of Tempol® and 0.14 g of Topanol® A in dissolved form are added. After the reaction and water addition have ended, 1600 g of aqueous acrylic acid-containing methoxypolyethylene glycol 2000 acrylate solution are obtained.

Analytical Data:

OH number of the 10 g sample, consisting of methoxypolyethylene glycol 2000: 26 mg KOH/g

| End product: | Water content: 49% (Karl-Fischer titration)<br>Acid number: 24 mg KOH/g (titration)<br>Hydroxyl number (calculated on dry substance): 2 mg KOH/g |
|---|---|

Example 8

As Example 1, except that, instead of the sodium methoxide solution and the methanol, 4.1 g of potassium tert-butoxide and 27 g of dry n-butanol are used. Reaction is effected with 971 g of propylene oxide in 4 h. After the sampling, 115 g of methacrylic anhydride which contains 4.5 g of HQME, 0.11 g of Tempol® and 0.23 g of Topanol® A in dissolved form are added. After the reaction and water addition have ended, 2200 g of aqueous methacrylic acid-containing butoxypolypropylene glycol 2000 methacrylate solution are obtained.

Analytical Data:

OH number of the 10 g sample, consisting of butoxypolypropylene glycol 2000: 25 mg KOH/g

| End product: | Water content: 50% (Karl-Fischer titration)<br>Acid number: 24 mg KOH/g (titration)<br>Hydroxyl number (calculated on dry substance): 1.2 mg KOH/g |
|---|---|

Example 9

As Example 8, except that reaction is effected successively with 486 g of ethylene oxide and 486 g of propylene oxide in a total of 4 h. After the sampling, 115 g of methacrylic anhydride which contains 4.5 g of HQME, 0.11 g of Tempol® and 0.23 g of Topanol® A in dissolved form are added. After the reaction and water addition have ended, 2200 g of aqueous methacrylic acid-containing butoxypolyethylene polypropylene glycol 2000 methacrylate solution are obtained.

Analytical Data:

OH number of the 10 g sample, consisting of butoxypolyethylene polypropylene glycol 2000: 28 mg KOH/g

| End product: | Water content: 50% (Karl-Fischer titration)<br>Acid number: 23.5 mg KOH/g (titration)<br>Hydroxyl number (calculated on dry substance): 1 mg KOH/g |
|---|---|

Example 10

As Example 1, except using 18 g of NM30 solution and 261 g of C16-18 alcohol (Hydrenol® D, Cognis). At 100° C./150 mbar, the methanol fraction is drawn off, then the mixture is blanketed with nitrogen and reacted with 1100 g of ethylene oxide. After the sampling, 229 g of methacrylic anhydride which contains 6.3 g of HQME, 0.16 g of Tempol® and 0.46 g of Topanol® A in dissolved form are added. After the reaction and water addition have ended, 3190 g of aqueous methacrylic acid-containing alkoxypolyethylene glycol 1100 methacrylate solution are obtained.

Analytical Data:

OH number of the 10 g sample, consisting of $C_{16-18}$ alkoxypolyethylene glycol methacrylate 1100: 50 mg KOH/g

| End product: | Water content: 51% (Karl-Fischer titration)<br>Acid number: 40 mg KOH/g (titration)<br>Hydroxyl number (calculated on dry substance): 1.8 mg KOH/g |
|---|---|

Example 11

Noninventive, Comparative Example

Separate ethoxylation and methacrylation according to the prior art

Apparatus: 2 l Büchi jacketed glass autoclave with manometer, mechanical stirrer, internal Pt 100 temperature sensor, inlet tube and oil circulation thermostat.

The reactor is evacuated, filled with nitrogen and charged with 6.6 g of a 30% solution of sodium methoxide in methanol (NM 30, Degussa AG). Another 6 g of dry methanol are added, the mixture is heated to 100° C. and 756 g of ethylene oxide are pumped in within 2 h, such that a pressure of 6 bar is not exceeded. Thereafter, the reaction is allowed to continue at this temperature for a further 0.5 h. The mixture is cooled to 80° C. and unconsumed ethylene oxide is drawn off under reduced pressure (approx. 150 mbar) (duration: approx. 0.5 h). The methoxypolyethylene glycol 2000 formed is withdrawn via the bottom valve and a sample (10 g) is taken for hydroxyl number determination. Yield: 753 g (98% of theory)

OH number of the 10 g sample, consisting of methoxypolyethylene glycol 2000: 28 mg KOH/g The product is introduced into a 2 l round-bottomed flask with stirrer and reflux condenser with 83.6 g of methacrylic anhydride which comprises 3.4 g of hydroquinone monomethyl ether (HQME) and 0.17 g of 2,6-dimethyl-4-tert-butylphenol (Topanol® A) and 0.08 g of 4-hydroxy-2,2,6,6-tetramethylpiperidine 1-oxyl (Tempol®) in dissolved form, and heated to 90° C. at standard pressure while passing air through slowly. After 6 h, a sample is taken and, according to NMR spectroscopy, has a conversion of 90%. After a total of 8 h at 90° C., the mixture is cooled to room temperature, and the reaction product is withdrawn, weighed and admixed with the same amount of water. 1650 g of an aqueous methacrylic acid-containing methoxypolyethylene glycol 2000 methacrylate solution are obtained.

| End product: | Water content: 49% (Karl-Fischer titration)<br>Acid number: 24 mg KOH/g (titration)<br>Hydroxyl number (calculated on dry substance): 1 mg KOH/g |
|---|---|

Example 12

As Example 1, except using 1.44 g of sodium hydroxide and 60 g of triethylene glycol monomethyl ether. After heating to 100° C., water of reaction formed is drawn off under reduced pressure for 0.5 h. 624 g of ethylene oxide are then pumped in within 1.5 h. After the sampling, 83.6 g of methacrylic anhydride which contains 3.4 g of hydroquinone monomethyl ether (HQME) and 0.17 g of 2,6-dimethyl-4-tert-butylphenol (Topanol® A) and 0.08 g of 4-hydroxy-2,2,6,6-tetramethylpiperidine 1-oxyl (Tempol®) in dissolved form are introduced into the reactor at standard pressure while slowly passing air through at 90° C. for 6 h.

After cooling to room temperature, the reaction product is withdrawn, weighed and admixed with the same amount of water. 1500 g of an aqueous methacrylic acid-containing methoxypolyethylene glycol 2000 methacrylate solution are obtained.

OH number of the 10 g sample consisting of methoxypolyethylene glycol 2000: 29 mg KOH/g

| End product: | Water content: 51% (Karl-Fischer titration)<br>Acid number: 26 mg KOH/g (titration)<br>Hydroxyl number (calculated on dry substance): 1.5 mg KOH/g |
|---|---|

Example 13

As Example 1, except that the stabilizer added to the methacrylic anhydride is only 3.4 g of Topanol A®. The resulting 1680 g of a methoxypolyethylene glycol 2000 methacrylate solution in water contain 1520 ppm of Topanol A®, i.e. of the 2000 ppm of stabilizer used, only a small portion has been consumed by side reactions.

Example 14

Comparative Example

As Example 1, except that the stabilizer added to the methacrylic anhydride is only 0.85 g of phenothiazine (500 ppm based on aqueous product solution). The resulting 1690 g of a methoxypolyethylene glycol 2000 methacrylate solution in water contain 490 ppm of phenothiazine (determined by liquid chromatography). After 1 week of storage in diffuse daylight, the product solution has polymer fractions (determined by NMR spectroscopy).

Example 15

Comparative Example

As Example 1, except that the stabilizer added to the methacrylic anhydride is 0.85 g of 2,6-di(tert-butyl)-4-methylphenol (Topanol O®) (500 ppm based on aqueous product solution). The resulting 1700 g of a methoxypolyethylene glycol 2000 methacrylate solution in water contain 480 ppm of Topanol O® (determined by liquid chromatography). The product solution is stable but is cloudy.

Example 16

Comparative Example

As Example 1, except that the stabilizer added to the methacrylic anhydride is 0.85 g of Tempol® (500 ppm based on aqueous product solution). The resulting methoxypolyethylene glycol 2000 methacrylate solution in water contains 50 mol % of polymer (determined by NMR spectroscopy).

The invention claimed is:

1. A process for preparing an alkoxypolyoxyalkylene (meth)acrylate without isolation of intermediates comprising:
  initially charging at least one metal alkoxide having the formula MetOR$^{10}$ to a reactor;
  adding at least one alcohol having the formula

R$^{12}$OH to the reactor;
  pumping at least one alkylene oxide of the formula (VI) into the reactor and
  reacting the at least one alkylene oxide of the formula (VI) with the metal alkoxide having the formula MetOR$^{10}$ to form an intermediate reaction product;

$$\underset{\substack{11\text{R} \\ 11\text{R}}}{\overset{\text{O}}{\triangle}}\underset{\substack{\text{R}^{11} \\ \text{R}^{11}}}{} \quad (\text{VI})$$

and
  directly adding (meth)acrylic anhydride to the reactor; and
  reacting the (meth)acrylic anhydride with the intermediate reaction product to obtain the alkoxypolyoxyalkylene (meth)acrylate;
  wherein
  Met is lithium, sodium, potassium, rubidium or cesium,
  R$^{110}$ is a linear or branched alkyl radical,
  the R$^{11}$ radicals are each independently hydrogen or a linear or branched alkyl radical having 1 to 8 carbon atoms, and the R$^{11}$ radicals are same or different,
  R$^{12}$ is a linear or branched, optionally alkoxylated alkyl radical having 1 to 18 carbon atoms,
  a molar mass of R$^{12}$ is less than a molar mass of the alkoxypolyoxyalkylene (meth)acrylate.

2. The process according to claim 1, wherein R$^{10}$ is methyl, ethyl or tert-butyl.

3. The process according to claim 1, wherein R$^{10}$ and R$^{12}$ are the same alkyl radical.

4. The process according to claim 1, wherein the at least one alkylene oxide of the formula (VI) is ethylene oxide and/or propylene oxide.

5. The process according to claim 1, wherein a stabilizer or a stabilizer mixture is present in the reacting of the (meth)acrylic anhydride with the reaction product to obtain the alkoxypolyoxyalkylene (meth)acrylate.

6. The process according to claim 5, wherein a weight ratio of (meth)acrylic anhydride:stabilizer or stabilizer mixture is in the range of 100:0.5-15.0.

7. The process according to claim 5, wherein
  a stabilizer mixture is present, and
  the stabilizer mixture comprises:
  at least one compound of the formula (I)

(I)

[Structure: phenol with OH at top, OR² at bottom, R¹ substituents at 2,3,5,6 positions]

wherein the R$^1$ radicals are each independently hydrogen, a linear or branched alkyl radical, an optionally substituted cycloalkyl radical, an optionally substituted aryl radical or a halogen, and
  R$^2$ is a linear or branched alkyl radical, an optionally substituted cycloalkyl radical or an optionally substituted aryl radical;
  at least one compound of the formula (II)

(II)

[Structure: phenol with OH, R³, R⁴, R⁵ substituents]

or of the formula (IV)

(IV)

[Structure: bisphenol with ester linkage: $[^{7}R-C-(CH_2)_o-C(=O)-O]_p-R^8$]

wherein the $R^3$, $R^4$ and $R^5$ radicals are each independently hydrogen, a linear or branched alkyl radical, an optionally substituted cycloalkyl radical, an optionally substituted aryl radical, a halogen or a radical of the formula (III)

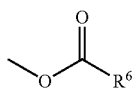
(III)

wherein $R^6$ is a linear or branched alkyl radical having 1 to 6 carbon atoms,
$R^7$ is hydrogen or a linear or branched alkyl radical, and
$R^8$ is a monovalent alkyl group or divalent alkylene group; and
at least one compound of the formula (V)

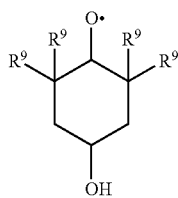
(V)

wherein the $R^9$ radicals are each independently a linear or branched alkyl radical or an optionally substituted cycloalkyl radical.

8. The process according to claim 7, wherein an amount of the stabilizer mixture is from 50 ppm to 5000 ppm, based on the sum of the masses of the reaction product, the (meth) acrylic anhydride and at least one alcohol.

9. The process according to claim 1, wherein a temperature of the reaction of the at least one alkylene oxide of the formula (VI) with the metal alkoxide having the formula $MetOR^{10}$ to form a reaction product is in the range of 60° C. to 150° C.

10. The process according to claim 9, wherein the reaction temperature is in the range of 90° C. to 110° C.

11. The process according to claim 1, wherein a molar ratio of the (meth)acrylic anhydride to the metal alkoxide is in a range of 1:1 to 3:1.

12. The process according to claim 1, wherein the reactants are dried and anhydrous conditions are maintained in the reactions.

13. A process for preparing an alkoxypolyoxyalkylene (meth)acrylate without isolation of intermediates comprising:
initially charging at least one metal alkoxide having the formula MetOH to a reactor;
adding at least one alcohol having the formula $R^{12}OH$ to the reactor to form a alcohol-metal hydroxide mixture;
dewatering the alcohol-metal hydroxide mixture;
pumping at least one alkylene oxide of the formula (VI) into the reactor and
reacting the at least one alkylene oxide of the formula (VI) with the dewatered alcohol-metal hydroxide mixture to form an intermediate reaction product;

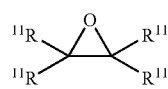
(VI)

directly adding (meth)acrylic anhydride to the reactor; and
reacting the (meth)acrylic anhydride with the intermediate reaction product to obtain the alkoxypolyoxyalkylene (meth)acrylate;
wherein
Met is lithium, sodium, potassium, rubidium or cesium,
$R^{110}$ is a linear or branched alkyl radical,
the $R^{11}$ radicals are each independently hydrogen or a linear or branched alkyl radical having 1 to 8 carbon atoms, and the $R^{11}$ radicals are same or different,
$R^{12}$ is a linear or branched, optionally alkoxylated alkyl radical having 1 to 18 carbon atoms,
a molar mass of $R^{12}$ is less than a molar mass of the alkoxypolyoxyalkylene (meth)acrylate.

14. The process according to claim 13, wherein a molar ratio of the (meth)acrylic anhydride to the metal hydroxide is in a range of 1:1 to 3:1.

15. The process according to claim 13, wherein the reactants are dried and anhydrous conditions are maintained in the reactions.

* * * * *